United States Patent [19]

Caupin et al.

[11] Patent Number: 5,416,116
[45] Date of Patent: May 16, 1995

[54] PEDICULICIDAL MEDICAMENTS COMPRISING DERIVATIVES OF UNDECYLENIC/UNDECANOIC ACIDS

[75] Inventors: Henri-Jean Caupin, Versailles; Aimë Menassa, Paris, both of France

[73] Assignees: Elf Atochem S.A., Puteaux; Delta Agro Industries, Paris, both of France

[21] Appl. No.: 261,213

[22] Filed: Jun. 15, 1994

Related U.S. Application Data

[63] Continuation of Ser. No. 905,368, Jun. 19, 1992, abandoned.

[30] Foreign Application Priority Data

Jun. 27, 1991 [FR] France .................. 91 07974
May 20, 1992 [FR] France .................. 92 06149

[51] Int. Cl.⁶ ............................ A61K 31/20
[52] U.S. Cl. ................................. 514/560
[58] Field of Search ................. 514/558, 560

[56] References Cited

U.S. PATENT DOCUMENTS

| | | | |
|---|---|---|---|
| 3,702,360 | 11/1972 | Graham | 424/288 |
| 4,147,800 | 4/1979 | Singer et al. | 424/312 |
| 5,017,615 | 5/1991 | Workman | 514/560 |

FOREIGN PATENT DOCUMENTS

| | | |
|---|---|---|
| 0279523 | 1/1988 | European Pat. Off. . |
| 0392806 | 4/1990 | European Pat. Off. . |
| 2377154 | 1/1978 | France . |
| 1792467 | 11/1971 | Germany . |
| 2263509 | 7/1974 | Germany . |
| 2222774 | 3/1990 | United Kingdom . |

OTHER PUBLICATIONS

Chemistry of Insecticides and Fungicides, Apr. 1945, D. E. H. Frear, pp. 125–130.
Chemical Abstracts, vol. 98, No. 25, Jun. 20, 1983, Abstract No. 211570X, p. 219.
Chemical Abstracts, vol. 50, 1956, Abstract Nos. 13358E–13359B.

*Primary Examiner*—Raymond Henley, III
*Assistant Examiner*—Phyllis G. Spivack
*Attorney, Agent, or Firm*—Burns, Doane, Swecker & Mathis

[57] ABSTRACT

Methods for the treatment of pediculosis are disclosed comprising applying a pediculicidally effective amount of at least one metal salt or ester of undecylenic acid in combination with a pharmaceutically acceptable topical carrier therefor.

15 Claims, No Drawings

PEDICULICIDAL MEDICAMENTS COMPRISING DERIVATIVES OF UNDECYLENIC/UNDECANOIC ACIDS

This application is a continuation of application Ser. No. 07/905,368, filed Jun. 29, 1992, now abandoned.

BACKGROUND OF THE INVENTION

1. Field of the Invention

The present invention relates to the use of certain ionic or non-ionic derivatives of undecylenic acid or undecanoic acid for eliciting a pediculicidal response.

This invention also relates to novel pharmaceutical compositions well suited for treating infestations caused by pedicular parasites.

2. Description of the Prior Art

The origin of pediculosis is lice, a parasite exclusive to man and which is essentially classified into three species:

(1) *Pediculus humanus*, var. *capitis*, or head louse,
(2) *Pediculus humanus*, var. *corporis*, or body louse,
(3) *Phtirius inguinalis*, or pubic louse.

Cases of pediculosis which are quite frequent, both in their endemic and epidemic forms, not only cause irritation and lesions from the resulting scratching, but lice are also vectors of certain disease states such a exanthematic or epidemic thyphus and recurrent fever.

Representative currently employed pediculicides, which are indeed polyvalent anti-parasitic agents comparable to insecticides employed for agricultural treatments, uses include, in particular, compounds of the organochloride or organophosphide family as well as the pyrethrins. Such compounds are variously formulated, notably as powders, lotions, shampoos or sprays. Each of these forms presents advantages and disadvantages. Thus, powders which, a priori are less toxic and are easy to use require a special item of headwear to be worn. Lotions, which are easy to apply and homogeneous, require prolonged contact and rinsing and can, moreover, because of the fact that they tend to run, promote irritation of the mucous membranes. Shampoos promote adverse effects because of the detergent included therein and they also require a relatively long contact time. Aerosols elicit a dissolving action on the lice and their eggs, but they do not permit controlled application, and, moreover, they can initiate certain eye irritations.

The pediculicidal compositions to date generally used include the following compounds:

(i) DDT (dichlorodiphenyltrichloroethane), which is an irritant, promotes changes in blood composition and number of blood cells, as well as affecting the hepatic and central nervous systems;

(ii) Hexachlorohexane and lindane, which are irritating to the skin, the mucous membranes and the eyes and for which certain intoxications have been indicated (vomiting, diarrhea, hyper-excitability, convulsions, acute pulmonary oedema, coma);

(iii) Natural or synthetic pyrethrins, such as bioallethrine, bioresmethrine, neopyramine, sumithrine, D-phenothrine, which can engender allergies and are sometimes irritating;

(iv) Benzyl benzoate and malathion, which have an irritating effect on the eyes and the scalp.

The incidents indicated are relatively rare and are practically non-existent under normal conditions of use, and have essentially occurred in infants. The have nevertheless occurred and hence can signify serious risks. In addition to such risks, current products frequently elicit skin irritations.

Such existing products suffer from the added disadvantage of displaying scant ovicide activity, namely, they are only slightly active on the eggs of lice (nits). Indeed, the currently employed compositions do not permit infestations by pedicular parasites to be combatted effectively, whether they be in the adult or larva (egg) state.

SUMMARY OF THE INVENTION

Accordingly, a major object of the present invention is the provision of novel pediculicidal compositions which are active against eggs (nits) and adult lice which additionally are based on natural products and which, furthermore, are innocuous to patients, both humans and higher animals. Cases of pediculosis caused by pedicular infestation can thus be avoided.

Briefly, the present invention features the use of a therapeutically effective amount of one or more non-ionic lipophilic and/or ionic hydrophilic derivatives of undecylenic acid or undecanoic acid to provide a pediculicidal medicament for treating infestations by pedicular parasites.

DETAILED DESCRIPTION OF THE PREFERRED EMBODIMENTS OF THE INVENTION

More particularly according to the present invention, in one embodiment thereof, the non-ionic lipophilic derivatives comprise the esters of undecylenic or undecanoic acid with a $C_1$-$CA_{16}$ mono-alcohol containing no other OH group than that which reacts with the COOH group of the undecylenic or undecanoic acid.

In a preferred embodiment of the invention, the mono-alcohol has from 1 to 6 carbon atoms, and more preferably 1 or 2 carbon atoms.

Undecylenic acid, the formula of which is:

and the metallic salts thereof (such as the Ca, Cu, Na and Zn salts), as well as the methyl ester thereof, are known for certain applications as bactericides and fungicides for topical application. Notably, undecylenic acid has to date been employed for treating fungal infections of the skin, notably of the scalp and, more specifically, for the treatment of dermatophytosis due to the tinia worm. In this respect, no activity whatsoever on lice by undecylenic acid or salts thereof has been suggested in this art. Moreover, experiments conducted on hair have demonstrated the presence of undecylenic acid among the fatty acids of the hair. No correlation between the amount of undecylenic acid and combatting lice resulted from such experimentation.

Undecanoic acid, the formula of which is

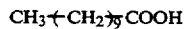

has not been employed for pharmacological applications.

The present invention also features novel pharmaceutical compositions and, notably, compositions suitable for treating pediculosis and containing nonionic lipophilic derivatives of undecylenic or undecanoic acid, e.g., the esters of undecylenic or undecanoic acid with a $C_1$–$C_{16}$ mono-alcohol containing no other OH group than that which reacts with the COOH group of the undecylenic or undecanoic acid. The pharmaceutical composition of the present invention may further comprise a pharmaceutically acceptable topical carrier therefor. A preferred pharmaceutical composition are preferably in power form or in the liquid state.

In another preferred embodiment of the invention, the mono-alcohol has from 1 to 6 carbon atoms, and, particularly preferably, 1 or 2 carbon atoms.

In accordance with another embodiment, the medicaments contain an organic solvent for the undecylenic acid ester.

Preferably, the solvent is a 30-70/70-30 alcohol/acetone mixture, and, particularly preferably, a 50/50 alcohol/acetone mixture.

In a preferred embodiment of the invention, the ionic hydrophilic derivatives comprise the metal salts, preferably the alkali metal or alkaline earth salts. Such metal salts include, for example, the Zn, Cu, Na, Ca and K salts, and the like.

The sodium salt is particularly preferred.

The subject pharmaceutical compositions can, in general, contain varying amounts of the active ingredient, depending on the infestation to be treated, patient-related factors, etc. In one preferred embodiment of the invention, however, the medicament comprises said non-ionic lipophilic or hydrophilic derivative in weight proportions on the order of 2% to 20% based on the total weight thereof.

In order to further illustrate the present invention and the advantages thereof, the following specific examples are given, it being understood that same are intended only as illustrative and in nowise limitative. In said examples to follow all parts and percentages are given by weight, unless otherwise indicated.

EXAMPLES

The therapeutic treatments were conducted by patting the afflicted area with compresses that had been thoroughly soaked with the particular compositions, solutions or suspensions.

EXAMPLE 1

A blind run carried out using water only provided the results reported in Table I below:

TABLE I

|  | Number of nits | % |
|---|---|---|
| Initial | 108 | 100 |
| Hatching | 66 | 61 |
| Survival | 64 | 59 |

EXAMPLE 2

This example, serving as a control, employed a non-ionic hydrophilic derivative of undecylenic acid, i.e., a monoundecylenate of glycerol in an aqueous solution containing 30% of this ester.

A test carried out using this composition provided the results reported in Table II which follows:

TABLE II

|  | Number of nits | % |
|---|---|---|
| Initial | 89 | 100 |
| Hatching | 54 | 61 |
| Survival | 53 | 60 |

The same tests carried out using the di-undecylenate of glycerol provided results essentially identical in percentage.

EXAMPLE 3

A test was carried out under the identical conditions of Example 2, but using an aqueous solution containing 30% of the undecylenate of PEG 400 provided the results reported in Table III below:

TABLE III

|  | Number of Nits | % |
|---|---|---|
| Initial | 103 | 100 |
| Hatching | 55 | 53 |
| Survival | 53 | 51 |

These results obtained using a solution containing a non-ionic hydrophilic derivative illustrated that it was not possible to attain better results than those obtained by means of a simple rinsing of the hair with water (Example 1).

EXAMPLE 4

In this example, a 50:50 alcohol/acetone solution was used as a control.

Application of this solution, under identical conditions, provided the following results:

TABLE IV

|  | Number of Nits | % |
|---|---|---|
| Initial | 116 | 100 |
| Hatching | 55 | 47 |
| Survival | 52 | 45 |

This solution provided results that were not significant, as only 50% of the nits were destroyed, which were comparable to the preceding examples.

EXAMPLE 5 AND 6

Lipophilic derivatives, i.e., methyl undecylenate (Example 5), and ethyl undecylenate (Example 6) in 10% solution in a 50/50 alcohol/acetone mixture were employed.

The results reported in Table V below were obtained:

TABLE V

|  | Methyl undecylenate | | Ethyl undecylenate | |
|---|---|---|---|---|
|  | No. of nits | % | No. of nits | % |
| Initial | 92 | 100 | 92 | 100 |
| Hatching | 0 | 0 | 6 | 6.5 |
| Survival | 0 | 0 | 0 | 0 |

The derivatives according to the present invention were thus notably active, which was both surprising and unexpected.

EXAMPLE 7

For this test, a hydrophilic ionic derivative, i.e., the sodium salt of undecylenic acid, was employed. The test was carried out, firstly, on 137 eggs (nits) from 2 to 5 days old (Table VI) and on 25 adult lice aged from 18 to 20 days (Table VII). Moreover, in the test on lice, the percentage of insects that were feeding—an estimation of survival—was measured. Controls used were a water and a dry control.

TABLE VI

| | Invention | | Water control | | Dry Control | |
|---|---|---|---|---|---|---|
| | Number | % | Number | % | Number | % |
| Hatching: % | 0 | 0 | 74 | 42 | 83 | 73.5 |
| Living: % | — | — | 31 | 87 | 61 | 82 |

Hatching = % hatching
Living = % of hatched insects that were feeding.

TABLE VII

| | Invention | | | Controls (water and dry) | | |
|---|---|---|---|---|---|---|
| | Number | % | Living | Number | % | Living |
| Mortality | 25 | 100 | 0 | 0 | 0 | 25 |

It was hence observed by comparing the results reported in the various tables that:

(a) Solutions or suspensions based on hydrophilic derivatives of undecylenic acid, such as the mono- or di-undecylenate of glycerol or the undecylenate of PEG 400, did not provide an extent of destruction of nits and lice higher than that attained by a simple rinsing with water;

(b) Non-ionic lipophilic derivatives or ionic hydrophilic derivatives of undecylenic acid in an alcohol/acetone solution or, respectively, in aqueous solution, provided results that were completely surprising and unexpected, namely, the complete or essentially complete destruction not only of the lice, but of the nits as well.

It will thus be appreciated that, based on the known state of this art, the use of non-ionic lipophilic or ionic hydrophilic derivatives of undecylenic acid (or undecanoic acid) unexpectedly elicits therapeutic responses which are radical, both as regards lice and nits.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed:

1. A method for the therapeutic treatment of a mammalian organism afflicted with pediculosis, comprising applying a therapeutically effective amount of at least one alkali metal salt of undecylenic acid to the locus of such pedicular infestation.

2. The method of claim 1, wherein the alkali metal salt comprises a sodium salt of undecylenic acid.

3. The method of claim 1, wherein the undecylenic acid salt is applied in combination with a pharmaceutically acceptable topical carrier.

4. The method of claim 3, wherein the pharmaceutically acceptable carder comprises a liquid.

5. The method of claim 4, wherein the liquid pharmaceutically acceptable carrier comprises an alcohol/acetone mixture.

6. The method of claim 3, wherein the pharmaceutically acceptable carder comprises a solid.

7. The method of claim 1, wherein the therapeutically effective amount comprises from about 2 to about 20% by weight of at least one alkali metal salt of undecylenic acid.

8. A method for the therapeutic treatment of a mammalian organism afflicted with pediculosis, comprising applying a therapeutically effective amount of at least one ester of undecylenic acid with a monoalcohol having from 1 to 6 carbon atoms to the locus of said pedicular infestation.

9. The method of claim 8, wherein the monoalcohol comprises methylalcohol.

10. The method of claim 8, wherein the monoalcohol comprises ethylalcohol.

11. The method of claim 8, wherein the ester of undecylenic acid with a monoalcohol having from 1 to 6 carbon atoms is applied in combination with a pharmaceutically acceptable carrier.

12. The method of claim 11, wherein the pharmaceutically acceptable carrier comprises a liquid.

13. The method of claim 12, wherein the liquid pharmaceutically acceptable carder comprises an alcohol/acetone mixture.

14. The method of claim 11, wherein the pharmaceutically acceptable carrier comprises a solid.

15. The method of claim 8, wherein the therapeutically effective amount comprises from about 2 to about 20% by weight of at least one ester of undecylenic acid with a monoalcohol having from 1 to 6 carbon atoms.

* * * * *